(12) United States Patent
Smith

(10) Patent No.: US 10,792,507 B2
(45) Date of Patent: *Oct. 6, 2020

(54) VARIABLE SOUND SYSTEM FOR AUDIO DEVICES

(71) Applicant: Physio-Control, Inc., Redmond, WA (US)

(72) Inventor: Robert Eugene Smith, Lynwood, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/576,246

(22) Filed: Sep. 19, 2019

(65) Prior Publication Data

US 2020/0009395 A1    Jan. 9, 2020

Related U.S. Application Data

(63) Continuation of application No. 16/267,182, filed on Feb. 4, 2019, now Pat. No. 10,441,806, which is a
(Continued)

(51) Int. Cl.
| | | |
|---|---|---|
| *H03G 3/20* | (2006.01) | |
| *A61N 1/39* | (2006.01) | |
| *H03G 9/00* | (2006.01) | |
| *H03G 9/02* | (2006.01) | |
| *G10L 19/02* | (2013.01) | |

(Continued)

(52) U.S. Cl.
CPC .............. *A61N 1/3993* (2013.01); *A61N 1/39* (2013.01); *H03G 9/005* (2013.01); *H03G 9/02* (2013.01); *G10L 19/02* (2013.01); *G10L 21/02* (2013.01); *G10L 21/0332* (2013.01); *H03G 3/24* (2013.01); *H03G 3/32* (2013.01); *H03G 9/025* (2013.01); *H04R 2430/01* (2013.01)

(58) Field of Classification Search
CPC ... A61N 1/3993; G10L 21/0208; G10L 19/02; G10L 21/0332; G10L 21/02; H03G 3/32; H03G 9/025; H03G 9/005; H03G 3/20; H03G 9/02; H04R 25/554; H04R 2430/01
USPC .......... 381/107, 56, 57, 315, 94.2, 104, 103; 704/226, 200.1, E21.002; 700/94
See application file for complete search history.

(56) References Cited

U.S. PATENT DOCUMENTS

| | | |
|---|---|---|
| 4,454,609 A | 6/1984 | Kates |
| 5,790,671 A | 8/1998 | Cooper |

(Continued)

FOREIGN PATENT DOCUMENTS

WO    WO20060020427    2/2006

OTHER PUBLICATIONS

Unknown, The art and science of the Sound Lab, Blog, post, dated Aug. 5, 2013.

*Primary Examiner* — Vivian C Chin
*Assistant Examiner* — Ubachukwu A Okunukwe
(74) *Attorney, Agent, or Firm* — Lee & Hayes, P.C.

(57) ABSTRACT

A system capable of self-adjusting both sound level and spectral content to improve audibility and intelligibility of electronic device audible cues. Audible cues are stored as sound files. Ambient noise is detected, and the output of the audible cues is altered based on the ambient noise. Various embodiments include processed sound files that are more robust in noisy environments.

20 Claims, 8 Drawing Sheets

Related U.S. Application Data continuation of application No. 15/617,862, filed on Jun. 8, 2017, now Pat. No. 10,195,452, which is a continuation of application No. 14/526,108, filed on Oct. 28, 2014, now Pat. No. 9,713,728.

(60) Provisional application No. 61/897,136, filed on Oct. 29, 2013.

(51) Int. Cl.
    *H03G 3/32* (2006.01)
    *H03G 3/24* (2006.01)
    *G10L 21/02* (2013.01)
    *G10L 21/0332* (2013.01)

(56) References Cited

U.S. PATENT DOCUMENTS

| | | |
|---|---|---|
| 5,792,190 A | 8/1998 | Olson et al. |
| 6,301,502 B1 | 10/2001 | Owen et al. |
| 7,548,781 B2 | 6/2009 | Vaisnys et al. |
| 8,165,314 B2 | 4/2012 | Sawashi |
| 8,280,730 B2 | 10/2012 | Song et al. |
| 8,331,574 B2 | 12/2012 | Powers |
| 8,964,998 B1 | 2/2015 | McClain |
| 9,225,310 B1* | 12/2015 | Lukin .............. H03G 9/025 |
| 9,713,728 B2 | 7/2017 | Smith |
| 2008/0091416 A1 | 4/2008 | Kim |
| 2009/0092260 A1* | 4/2009 | Powers .............. A61N 1/3993 381/57 |
| 2010/0166225 A1* | 7/2010 | Watanabe .............. H03G 3/32 381/107 |
| 2010/0202622 A1* | 8/2010 | Hardee .............. H04M 19/044 381/57 |
| 2011/0125494 A1* | 5/2011 | Alves .............. G10L 21/0208 704/226 |
| 2011/0267180 A1 | 11/2011 | Ferringo et al. |
| 2012/0101819 A1* | 4/2012 | Heiman .............. H04R 1/1083 704/233 |
| 2013/0343585 A1* | 12/2013 | Bennett .............. H04R 25/554 381/315 |
| 2014/0219478 A1 | 8/2014 | Takahashi |

* cited by examiner

FIG. 1   DEFIBRILLATION SCENE

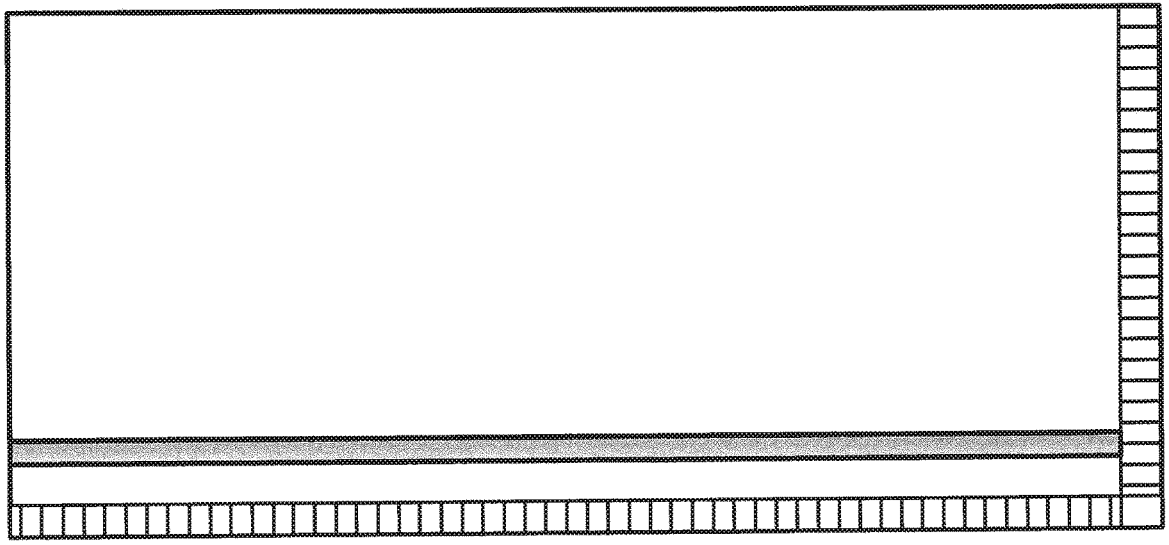
Fig. 6                                          Audible Cue
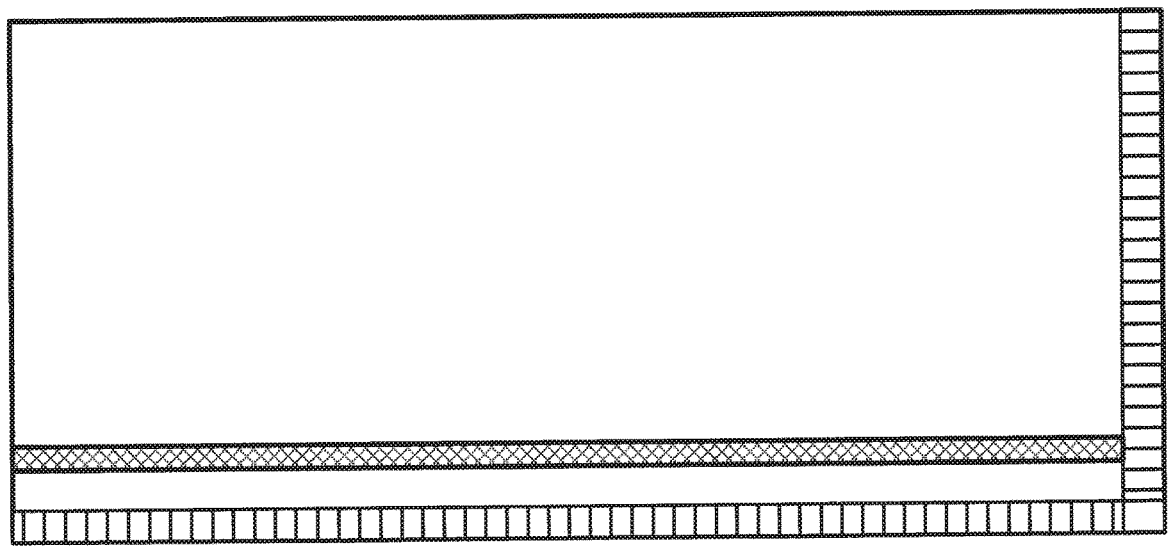
Fig. 7                                          Masking Signal Audible Cue
inaudible over
masking signal Alert Cue
with harmonics Alert Cute still audible despite Masking Signal Alert Cue with harmonics and Masking Signal with harmonics Alert Cue with
altered in accordance
with Critical Band
(CB) teachings CB Altered Alert Cue
with Masking Signal CB Altered Alert Cue
with Masking Signal
Having Harmonics

VARIABLE SOUND SYSTEM FOR AUDIO DEVICES

CROSS REFERENCE TO RELATED APPLICATIONS

This application is a continuation of application Ser. No. 16/267,182, filed Feb. 4, 2019, which is a continuation of U.S. application Ser. No. 15/617,862 filed on Jun. 8, 2017, now U.S. Pat. No. 10,195,452, issued on Feb. 5, 2019, which is a continuation of U.S. application Ser. No. 14/526,108 filed Oct. 28, 2014, now U.S. Pat. No. 9,713,728, which claims the benefit of and priority to U.S. Provisional Patent Application Ser. No. 61/897,136 filed on Oct. 29, 2013, titled "Variable Sound System For Medical Devices," the disclosures of which is hereby incorporated by reference for all purposes.

TECHNICAL FIELD

The disclosed subject matter pertains to the area of electronic devices.

BACKGROUND INFORMATION

The use of field-deployed medical devices, such as portable defibrillators, is achieving widespread acceptance. Such devices are designed to be used in high-stress environments by people who may not be well trained. Thus, the medical devices commonly provide audible cues to the user to guide the use of the medical device. However, such medical devices may be deployed in greatly disparate noise environments ranging from very quiet, such as an office setting, to very loud, such as a railroad station. Thus, the audible cues must compete with drastically different ambient sounds that interfere with the intelligibility of the audible cues.

Portable devices are also constrained by size, weight, and power limitations.

SUMMARY OF EMBODIMENTS

Disclosed is a system capable of self-adjusting both sound level and spectral content to improve audibility and intelligibility of medical device audible cues. Audible cues are stored as sound files. Ambient noise is detected, and the output of the audible cues is altered based on the ambient noise. Various embodiments include processed sound files that are more robust in noisy environments.

BRIEF DESCRIPTION OF THE DRAWINGS

FIG. 6 is a sample spectrogram illustrating a 440 Hz pure sine tone, representing an audible cue.

FIG. 7 is a spectrogram illustrating a 400 Hz masker signal.

DETAILED DESCRIPTION OF EMBODIMENTS

Generally described, embodiments are directed at discovering information about an ambient sound environment, such as sound level, or spectral content or both, and exploiting psycho-acoustic principles of the human auditory system to enhance the ability to distinguish intended audible cues from ambient noise. Specific embodiments exploit masking and critical bands in the basilar membrane. Combining a measurement of the ambient sound environment and a psycho-acoustically driven knowledge base of the spectrum, a sound source is chosen or modified as necessary to improve resistance to auditory masking, thereby improving the audibility of alerts and alarms, and intelligibility of voice prompts. Although particularly applicable to the area of portable medical devices, the disclosed subject matter has applicability to many other areas, such as the automotive industry, or the like.

Figure 1:
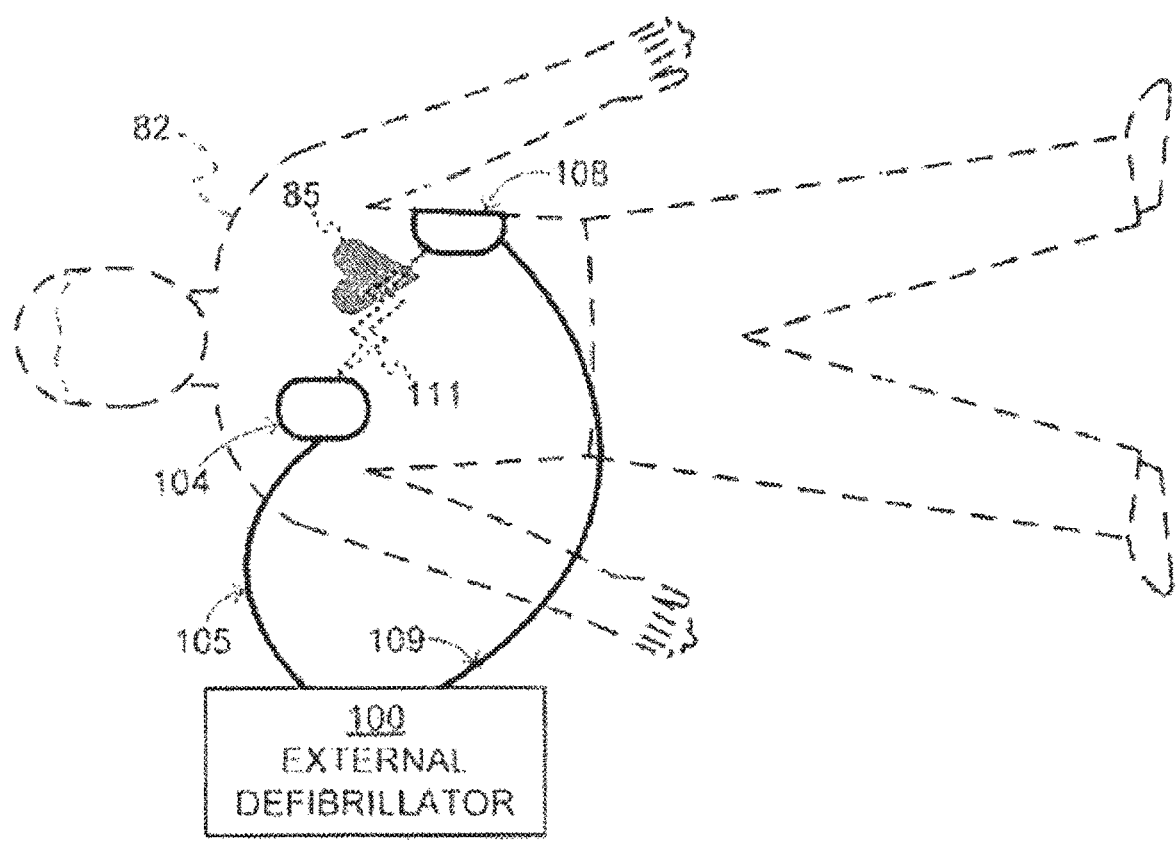
FIG. 1 is a diagram of a scene where an external defibrillator is used to save the life of a person.

FIG. 1 is a diagram of a defibrillation scene. A person 82 is lying supine. Person 82 could be a patient in a hospital, or someone found unconscious and turned on his or her back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82. Defibrillator 100 can be one of different types, each with different sets of features and capabilities. The set of capabilities of defibrillator 100 is determined by planning who would use it, and what training they would be likely to have.

In use, defibrillator 100 provides audible cues to inform the rescuer of the steps to properly operate defibrillator 100. However, the defibrillation scene may occur in any one of many different environments having greatly divergent audible characteristics. In other words, the defibrillation scene may occur in a relatively quiet indoor environment, or it may occur in a relatively loud outdoor environment, or anything in between. Operating in various noise environments poses problems for selecting the appropriate format to output the audible cues. In loud environments, the audible cues can be difficult to hear if too quiet. In quiet environments, the audible cues can be harsh on the ear and even quasi painful if too loud. Either case (quiet or loud environments) both result in degradation in speech intelligibility under the foregoing conditions. Disclosed are embodiments that enable the defibrillator 100 to automatically adjust the sound output of the audible cues based on the ambient noise environment.

Generally stated, when two sounds are closely related in time and frequency such that they are within a critical band of each other, the sound with the lower sound level will be masked by the one with the higher sound level. This phenomenon is illustrated with reference to the sample spectrograms of FIGS. 6-8. In the spectrograms, the "X" axis denotes time; 0 to 10 seconds. The "Y" axis represents frequency; 0 to 4000 Hz. Sound levels are represented by brightness on the spectrogram; brighter is higher sound level, darker is lower sound level. For simplicity of discussion, simple sounds will be presented. However, the concepts extend equally to complex sounds including music and speech.

Figure 8:
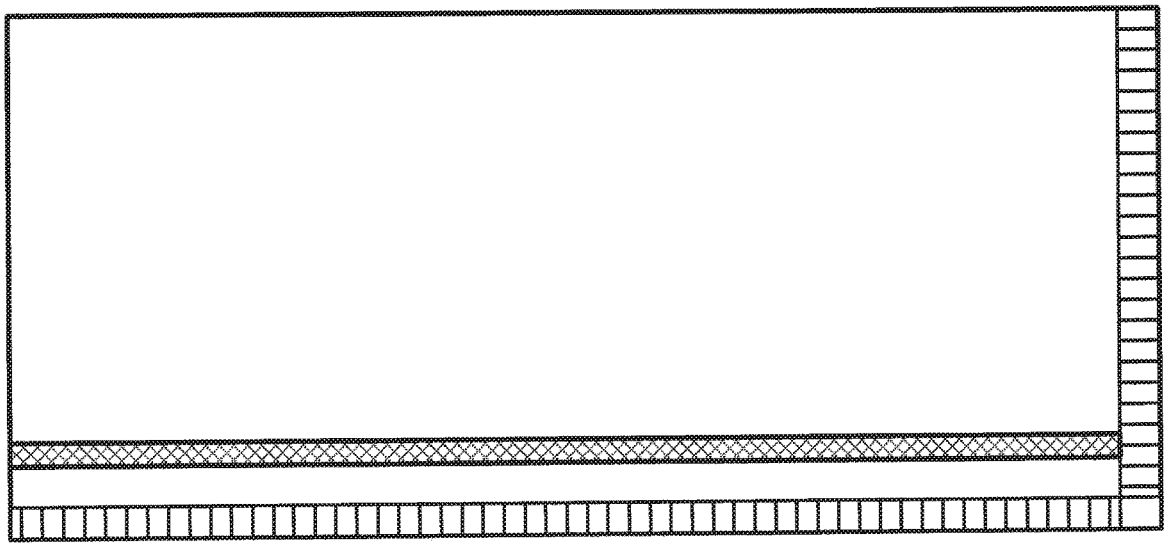
FIG. 8 is a sample spectrogram revealing that when presented together, the 400 Hz masking sound dominates the 440 Hz audible cue.

Referring briefly to FIG. 6, illustrated is a sample spectrogram showing a 440 Hz pure sine tone. This tone represents an audible cue (e.g., an alert) to be communicated to a user of a medical device. FIG. 7 is a spectrogram illustrating a 400 Hz masker signal. The masker signal will be the interfering ambient sound. FIG. 8 is a sample spectrogram revealing that when presented together, the 400 Hz masking sound dominates the 440 Hz audible cue. In this situation, the 440 Hz audible cue will not be audible over the masker signal. The embodiments shown in FIGS. 2 5 seek to ameliorate this situation and enhance intelligibility of audible cues output by a medical device.

Figure 2:
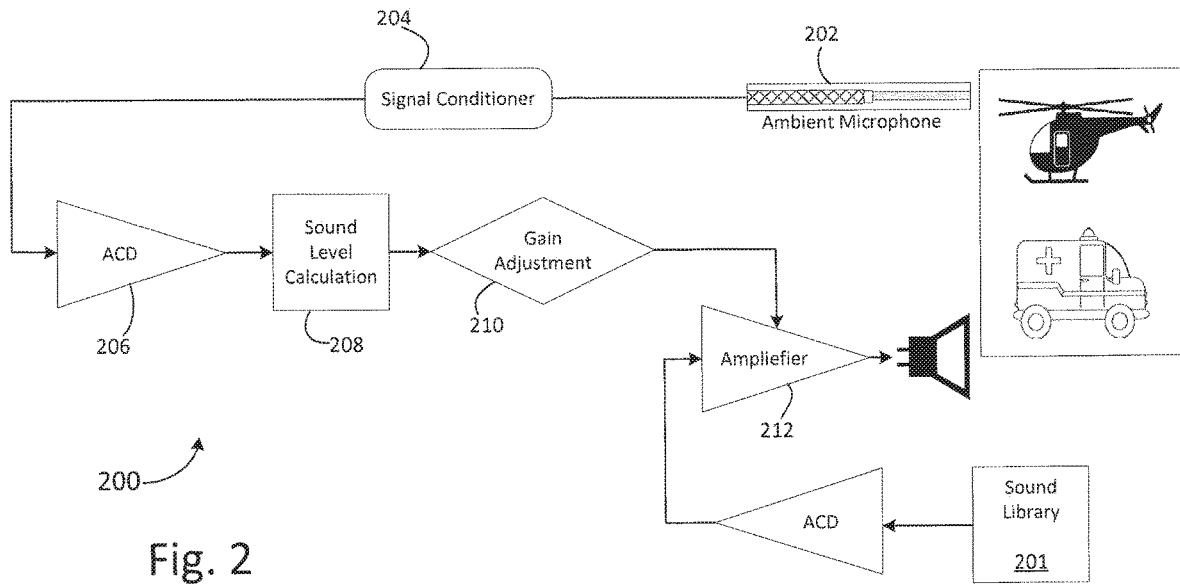
FIG. 2 is a functional block diagram generally illustrating core components of one basic embodiment.

FIG. 2 is a functional block diagram generally illustrating components of one basic embodiment. In this basic embodiment, a system 200 is implemented in a medical device and includes a microphone 202 to record the ambient noise being experienced in the environment and a library 201 of sound files which each represent audible cues. Each audible cue may be, in one implementation, a voice prompt or instruction for operating the medical device. In accordance with this embodiment, each sound file is processed to enhance intelligibility in loud environments. More specifically, the sound files may be processed to enhance harmonic signals of each audible cue, which serves to enhance the intelligibility of the audible cue, especially in louder environments.

However, such processing may result in an audible cue which sounds somewhat harsh in quiet environments. Thus, it is desirable to output the audible cues at a volume that does not irritate the operator's hearing. Illustrative processing methods are illustrated in FIGS. 9-14 and described below.

The sound recorded using the microphone 202 is conditioned using signal conditioner 204 and converted from an analog signal to a digital signal using ADC 206. A sound level calculation component 208 then detects the sound level (e.g., volume) of the noise in the ambient environment. Using the detected sound level, a gain adjustment is applied to an amplifier 212 thus adjusting the sound level of audible cues such that it is appropriate for the current environment.

In various implementations, the gain adjustment 210 could be either an analog or digital control, with the latter depicted in FIG. 2. While offering intelligent adjustment of the sound level, this version offers basic improvement in resistance to auditory masking by ambient sounds.

Figure 3:
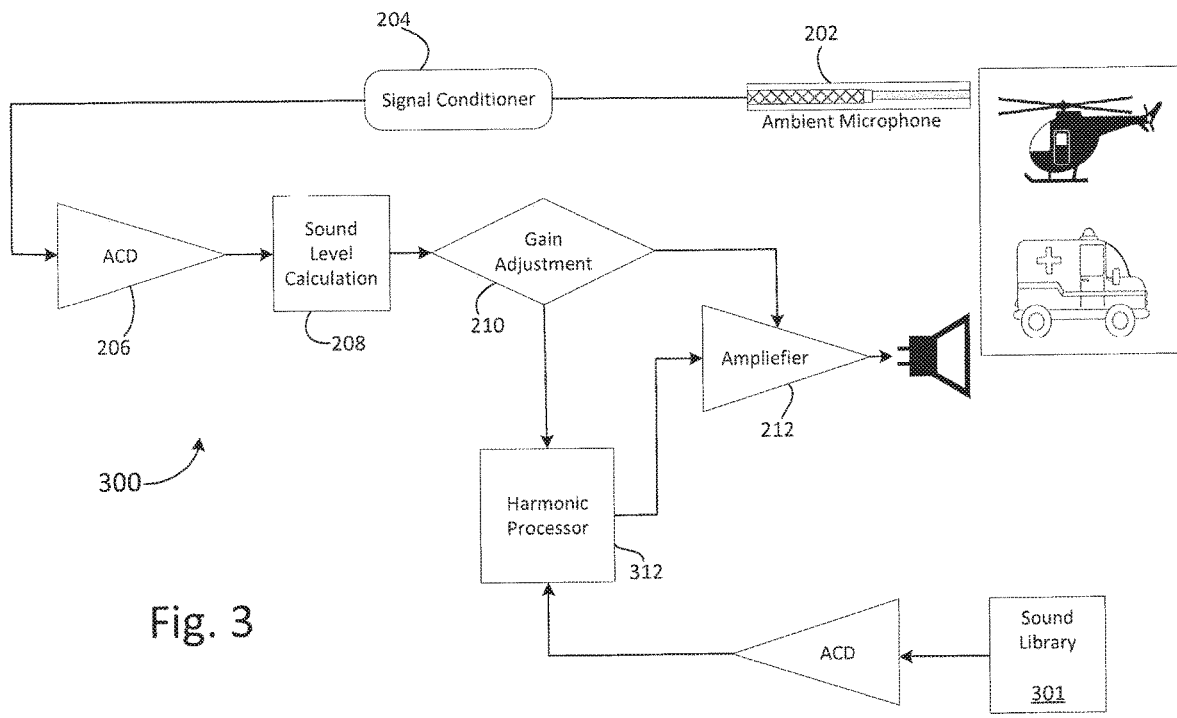
FIG. 3 is a functional block diagram illustrating components of a first alternative embodiment that improves on the basic embodiment of FIG. 1.

FIG. 3 is a functional block diagram illustrating components of a first alternative embodiment 300 that improves on the basic embodiment of FIG. 1. Generally stated, components shown in FIG. 3 operate in the same manner as similarly-labeled components shown in FIG. 2. However, the sound files in the sound library 301 of the first alternative embodiment are somewhat less processed than those in the sound library 201 of the basic embodiment. Accordingly, the audible cues sound somewhat less harsh in quiet environments at the expense of some loss in intelligibility in more noisy environments.

The first alternative embodiment operates largely in a similar manner as the basic embodiment described above. Thus, the sound level of the ambient noise of the environment is determined using a microphone 202 and sound level calculation component 208. However, the first alternative embodiment includes a harmonic processor 312 to add harmonically related frequency content to the audible cue to enhance intelligibility at higher sound levels. In other words, when the sound level calculation determines that the medical device is operating in a louder ambient sound level, the gain of the amplifier is increased to raise the sound level of the audible cue. In addition, the harmonic processor 312 dynamically alters the sound files to include harmonics that enhance the intelligibility of the audible cues in noisy environments. Accordingly, the audible cues sound less harsh in quiet environments where masking is less of a problem, but harshness is added (e.g., via third and fifth harmonics) to enhance intelligibility in a noisy environment.

As can be seen, the first alternative embodiment 300 produces more sound level when needed and also introduces harmonically-related spectral content to the output sound to enhance intelligibility at higher sound levels. The first alternative embodiment 300 improves greatly on the basic embodiment 200 for audibility in ambient noise.

Figure 4:
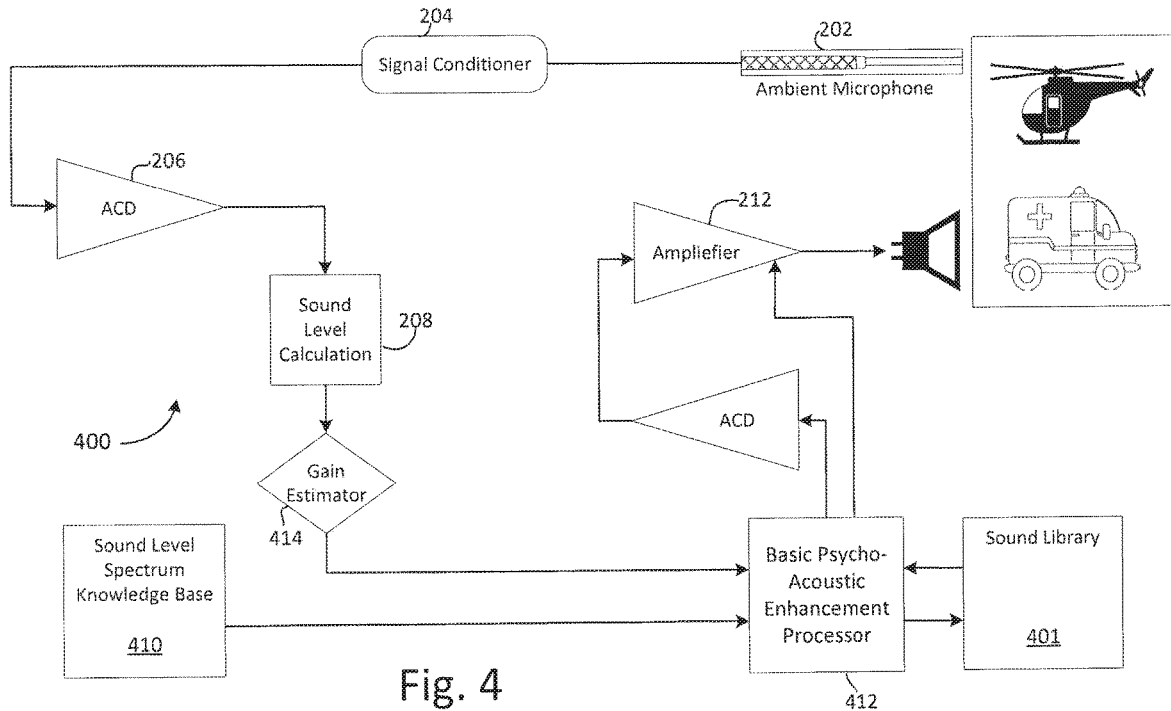
FIG. 4 is a functional block diagram illustrating components of a second alternative embodiment that improves on the first alternative embodiment of FIG. 3.

FIG. 4 is a functional block diagram illustrating components of a second alternative embodiment 400 that improves on the first alternative embodiment of FIG. 3. As above, components shown in FIG. 4 operate in the same manner as similarly-labeled components shown in FIGS. 2 and 3. However, the sound library 401 of the second alternative embodiment includes sound files that are more processed to enhance noisy-environment intelligibility (similar to the sound files used in the basic embodiment) and sound files that are less processed (similar to the sound files used in the first alternative embodiment). Accordingly, each of the audible cues may have at least two (but possibly more) corresponding sound files; at least one which sounds better in quieter environments and at least another that sounds better in louder environments. Of course, there may be certain audible cues for which alternative sound files are not necessary.

In accordance with this embodiment, a sound level spectrum knowledge base 410 is included which stores information about the spectral characteristics of typical maskers (i.e., competing noises which may mask the audible cues) in particular noise environments. In other words, based on prior evaluations and analysis, this embodiment incorporates a priori knowledge regarding particular noise contributors in various different ambient environments. In this manner, a basic psycho-acoustic enhancement processor (PAEP) 412 receives sound level information from the sound level calculation component 208 with an estimate of an appropriate gain that should be applied to a sound file based on the current ambient environment (via gain estimator 414).

The PAEP 412 uses the measurement of ambient sound level in combination with the knowledge base 410 of environmental noise levels. Based on (at least) those two inputs, the PAEP 412 determines which one of the several pre-processed sounds within sound library 401 best fit the ambient situation. Gain to the amplifier 212 may also be adjusted for enhanced use of the chosen pre-processed sound. The pre-processed sounds within library 401 have their spectral content adjusted based on one of many possible psycho-acoustic formulae for determining critical band frequencies of the basilar membrane. The spectral content of each specific sound is pre-processed to correspond with the various ambient sound level situations in the knowledge base 410.

Figure 5:
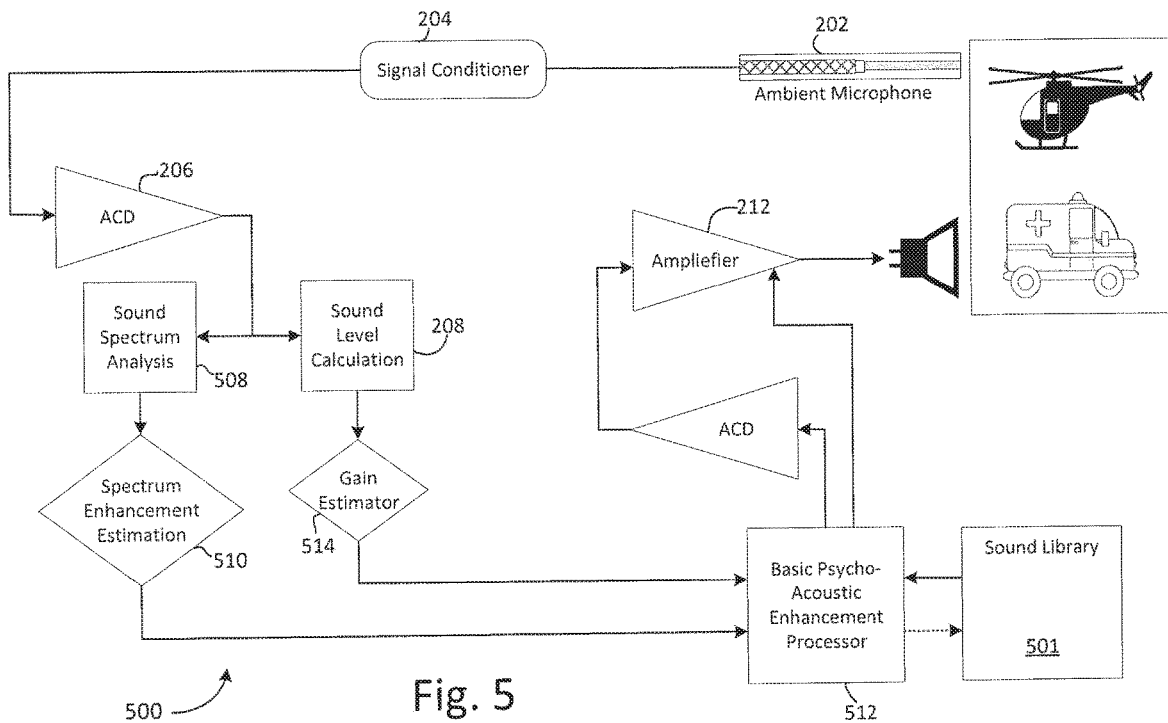
FIG. 5 a functional block diagram illustrating components of a third alternative embodiment that improves on the first and second alternative embodiments of FIGS. 3 and 4.

FIG. 5 a functional block diagram illustrating components of a third alternative embodiment 500 that improves on the first and second alternative embodiments of FIGS. 3 and 4. As above, components shown in FIG. 5 operate in the same manner as similarly-labeled components shown in FIGS. 2, 3 and 4. However, the sound library 501 of the third alternative embodiment may include sound files that are less processed to enhance noisy-environment intelligibility (similar to the sound files used in the first alternative embodiment). The sound library 501 of the third alternative embodiment may, but need not, also include sound files that are more processed (similar to the sound files used in the basic embodiment) for noisy-environment intelligibility.

The third alternative embodiment 500 includes a microphone 202 and ancillary components to detect both sound level (i.e., sound level calculation component 208) and sound spectrum (i.e., sound spectrum analysis component 508) of the ambient environment. Measurements of those two parameters are used to create estimates of predicted auditory masking of the device sounds, via a spectrum enhancement estimation component 510. A psycho-acoustic model of changes to the source sound spectrum emerges in real-time which may be used to make the source sounds more resistant to masking in the presence of potentially masking sounds of the ambient environment. In this embodiment, an advanced PAEP 512 predicts necessary changes to both sound level and spectral content dynamically to enhance the sound output of the medical device for a given environment.

In most embodiments, a hold function (not shown) should be used to prevent changes to the sensed ambient sound level and adjustments to the sound output during the period when the device is itself generating sound (e.g., while playing an audible cue). This avoids making inappropriate adjustments based on the device contribution to the ambient environment.

Sample spectrograms will now be presented to help illustrate the operation of the above-described embodiments. In particular, the sample spectrograms shown in FIGS. 9-14 provide guidance regarding the processing of sound files for use in the embodiments illustrated in FIGS. 2-5 and described above. As with FIGS. 6-8, the "X" axis denotes time; 0 to 10 seconds. The "Y" axis represents frequency; 0 to 4000 Hz. Sound levels are represented by brightness on the spectrogram; brighter is higher sound level, darker is lower sound level.

Figure 9:
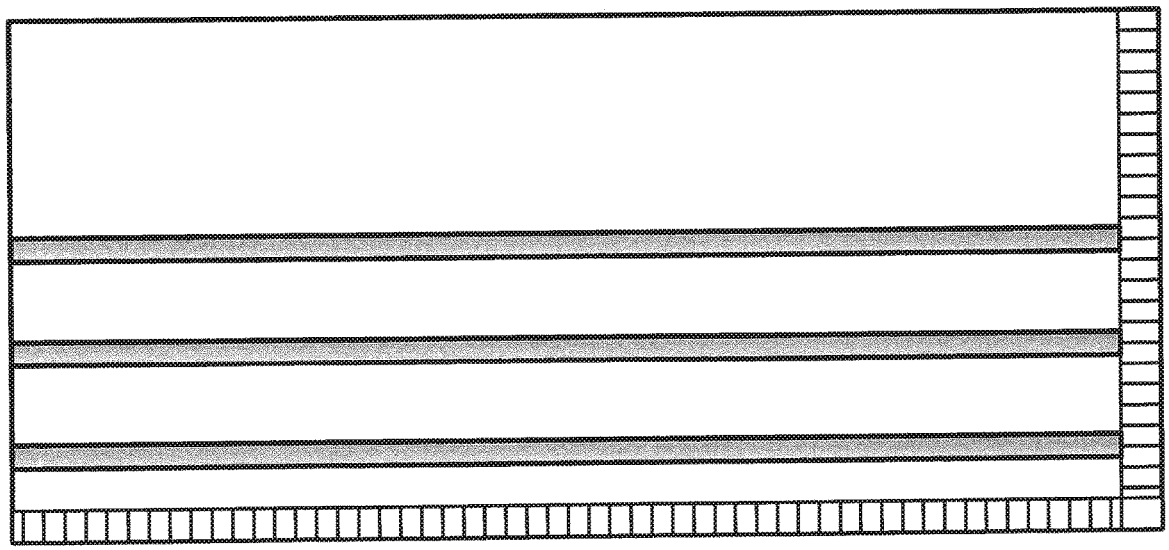
FIG. 9 is a sample spectrogram showing an audible cue processed to include harmonics of the audible cue.

FIG. 9 is a sample spectrogram showing an audible cue processed to include harmonics of the audible cue. Altering the sound spectrum of the audible cue such that energy is redistributed to the harmonics creates redundancies in non-overlapping auditory critical bands.

Figure 10:
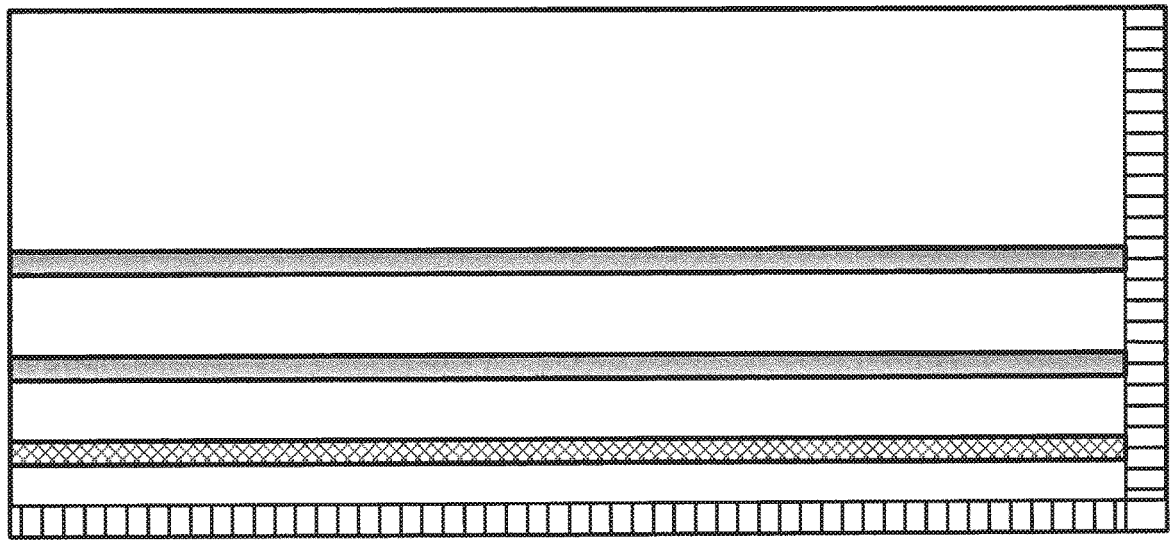
FIG. 10 is a sample spectrogram showing the altered audible cue of FIG. 9 in combination with the masker signal shown in FIG. 8.

FIG. 10 is a sample spectrogram showing the altered audible cue of FIG. 9 in combination with the masker signal shown in FIG. 8. As illustrated, when the 400 Hz single-frequency masker signal of FIG. 8 is presented with the altered audible cue of FIG. 9, the 400 Hz masker dominates the fundamental of the altered alert sound, but does not mask the higher harmonics. Thus, the altered alert audible cue is more robust to masking by a single frequency sound.

Figure 11:
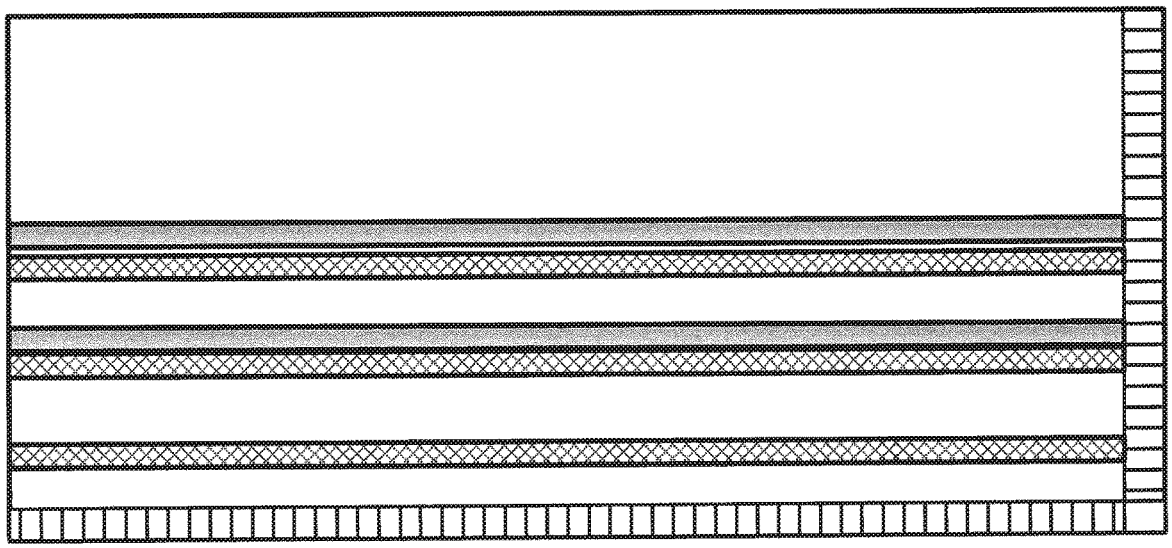
FIG. 11 is a sample spectrogram showing the altered audible cue of FIG. 9 in combination with a masker signal having harmonics.

FIG. 11 is a sample spectrogram showing the altered audible cue of FIG. 9 in combination with a masker signal having harmonics. As shown, if the altered audible cue may still be at risk of being hard to hear or even inaudible in the same environment as the masker signal with harmonic content. It will be appreciated that this depends on proximity of the masking sound harmonics to the altered audible cue harmonics and if they are both within a critical bandwidth of each other.

Figure 12:
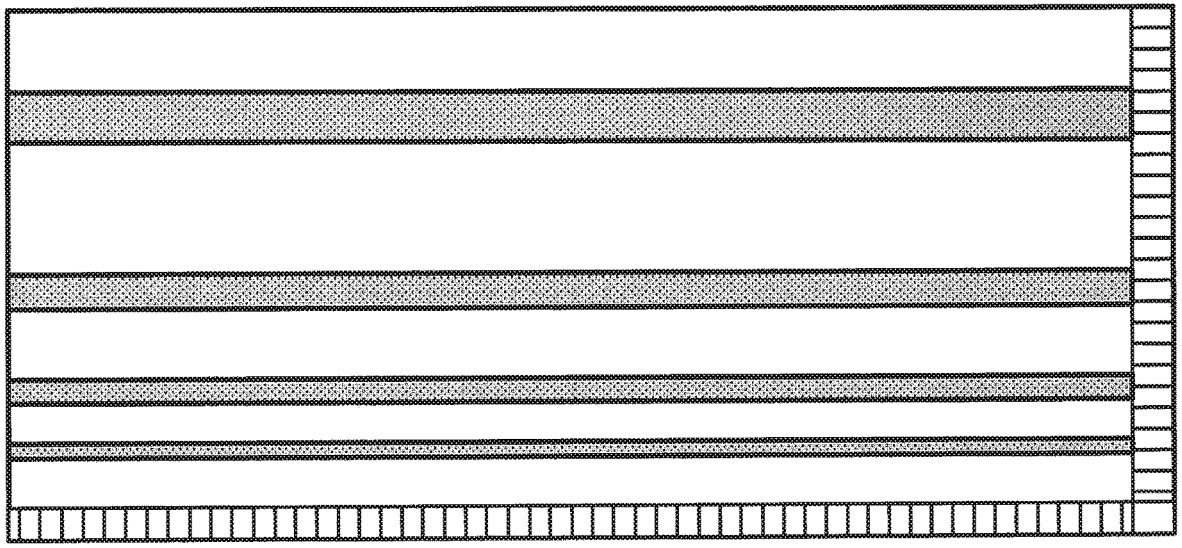
FIG. 12 is a sample spectrogram illustrating an audible cue altered in accordance with characteristics of the human auditory system.

FIG. 12 is a sample spectrogram illustrating an audible cue altered in accordance with characteristics of the human auditory system. More specifically, the adjustments to the audible cue are based on the psycho-acoustic concept of a Critical Bandwidth ("CB") that forms on the basilar membrane when stimulated. The basilar membrane is located within the cochlea in the inner ear. Generally stated, the critical bandwidth is the band of audio frequencies within which a second tone will interfere with the perception of a first tone by auditory masking. One such estimation of the critical bandwidth is presented below:

$$CB = 25 + 75[1 + 1.4(freq/1000)^2]^{0.69} Hz*$$

*Zwicker, Eberhard, Journal of Acoustical Society of America, November 1980

(This formula is but one example of many different equally-applicable formulae, as will be apparent to those skilled in the art.)

Figure 13:
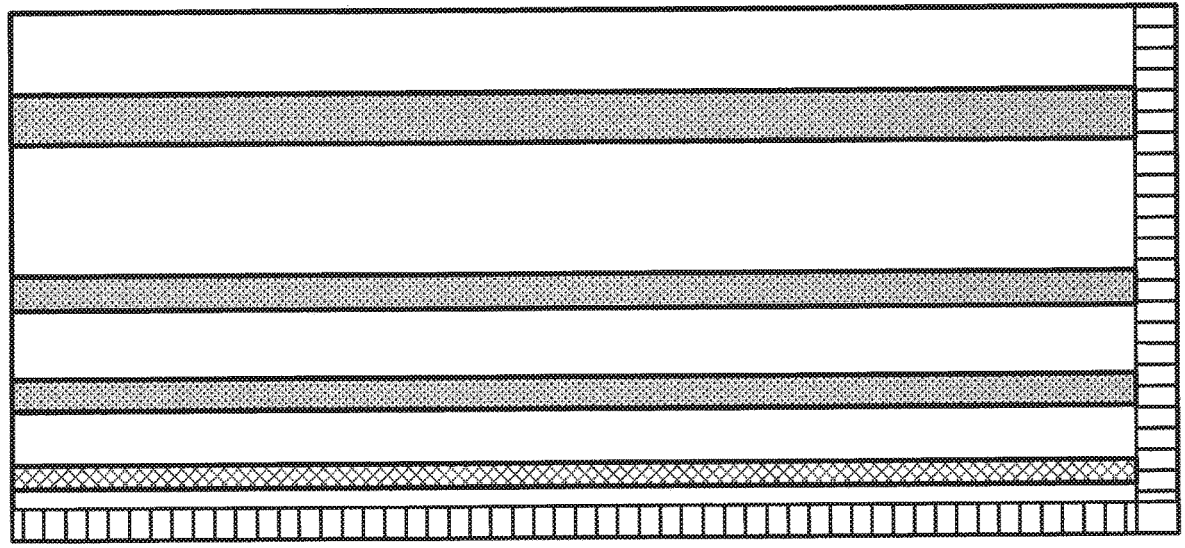
FIG. 13 is a sample spectrogram illustrating the critical band (described below) altered audible cue of FIG. 12 combined with the masking signal of FIG. 8.

FIG. 13 is a sample spectrogram illustrating the CB altered audible cue of FIG. 12 combined with the masking signal of FIG. 8. As is evident from FIG. 13, the CB altered audible cue is extremely robust to single frequency masking.

Figure 14:
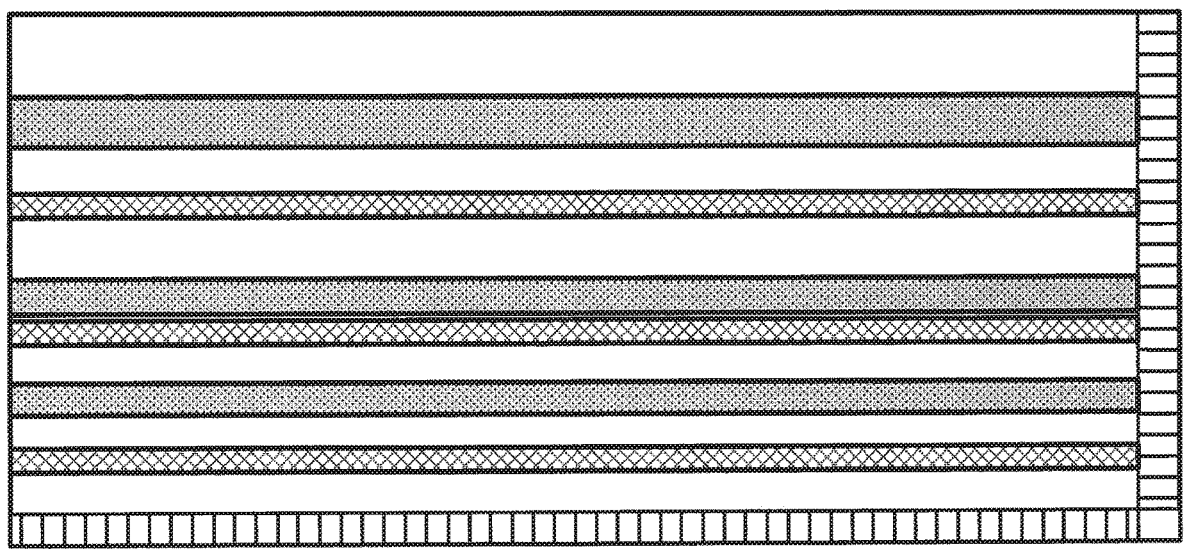
FIG. 14 is a sample spectrogram illustrating the critical band altered audible cue of FIG. 12 combined with the masking signal having harmonics.

FIG. 14 is a sample spectrogram illustrating the CB altered audible cue of FIG. 12 combined with the masking signal having harmonics. As is evident from FIG. 14, even when presented with a masking sound containing harmonic content, the CB altered audible cue remains audible as it is stimulating non-overlapping CBs of the basilar membrane and the spectral content is spread to avoid the harmonics of maskers.

In this description, numerous details have been set forth in order to provide a thorough understanding. In other instances, well-known features have not been described in detail in order to not obscure unnecessarily the description.

A person skilled in the art will be able to implement these additional embodiments in view of this description, which is to be taken as a whole. The specific embodiments disclosed and illustrated herein are not to be considered in a limiting sense. Indeed, it should be readily apparent to those skilled in the art that what is described herein may be modified in numerous ways. Such ways can include equivalents to what is described herein.

For example, in another embodiment for use in cars, trains, buses, planes, or other noisy environments in which audio announcements are made, a system may include a microphone configured to capture ambient noise; a sound library including a plurality of sound files, each sound file corresponding to an audible cue; an amplifier coupled to a speaker, the amplifier having a selectable gain and being configured to output each of the plurality of sound files over the speaker; a sound level detection component coupled to the microphone and configured to detect a sound level of the ambient noise; a sound spectrum detection component coupled to the microphone and configured to detect spectrum characteristics of the ambient noise; a sound spectrum analysis component coupled to the sound spectrum detection component and being configured to provide an estimate of an amount of gain to apply to tile amplifier based on an analysis of the spectral characteristics of the ambient noise; and a sound altering component configured to alter the selectable gain of tile amplifier based on the sound level of the ambient noise in conjunction with the estimate, or to alter harmonic content of the sound files based on the spectral characteristics of the ambient noise, or both.

In addition, various embodiments may be practiced in combination with other systems or embodiments. The following claims define certain combinations and subcombinations of elements, features, steps, and/or functions, which are regarded as novel and non-obvious. Additional claims for other combinations and subcombinations may be presented in this or a related document

What is claimed is:

1. An electronic device, comprising:
    a sound level calculation component configured to determine a sound level of an ambient environment of the electronic device;
    a sound spectrum analysis component configured to determine a sound spectrum of the ambient environment of the electronic device;
    an amplifier having an adjustable gain; and
    a processor configured to:
        determine the adjustable gain for the amplifier based on the sound level of the ambient environment;
        determine that a frequency band in receive the sound spectrum of the ambient environment overlaps a sound spectrum of an audible cue;
        alter the audible cue to comprise a harmonic of the sound spectrum of the audible cue, the harmonic being non-overlapping with the frequency band; and
        cause the electronic device to output, into the ambient environment, the altered audible cue with the applied adjustable gain.

2. The electronic device of claim 1, wherein the electronic device is portable.

3. The electronic device of claim 1, wherein the electronic device is integrated into a vehicle.

4. The electronic device of claim 1, further comprising a microphone configured to receive an ambient sound of the ambient environment, the sound level calculation component configured to determine the sound level of the ambient environment based on the ambient sound received by the microphone.

5. The electronic device of claim 1, wherein the processor is further configured to:
    select the audible cue from a sound library, the audible cue being selected based on the sound level of the ambient environment and the sound spectrum of the ambient environment.

6. The device of claim 5, wherein the audible cue comprises a loud environment audible cue or a quiet environment audible cue, and wherein the processor is further configured to select either the loud environment audible cue or the quiet environment audible cue based, at least in part, on one or both of the sound level of the ambient environment and the sound spectrum of the ambient environment of the electronic device.

7. The electronic device of claim 1, wherein the audible cue comprises a predetermined sound file.

8. The electronic device of claim 1, wherein the sound spectrum of the ambient environment comprises a harmonic of the frequency band, and wherein the harmonic of the sound spectrum of the audible cue is non-overlapping with the harmonic of the frequency band.

9. The electronic device of claim 1, wherein the audible cue comprises speech.

10. An electronic device, comprising:
    a microphone configured to receive audio in an ambient environment of the electronic device;
    a sound level calculation component configured to determine a sound level of the ambient environment of the electronic device based on the received audio in the ambient environment;
    a sound spectrum analysis component configured to determine a sound spectrum of the received audio in the ambient environment of the electronic device;
    an amplifier having an adjustable gain;
    a sound library having multiple audible cues that each comprise user instructions; and
    a processor configured to:
        receive the sound level of the ambient environment of the electronic device from the sound level calculation component;
        determine an ambient gain value for the amplifier based on the received audio;
        cause the amplifier to adjust the adjustable gain to the ambient gain value;
        receive the sound spectrum of the ambient environment of the electronic device from the sound spectrum analysis component;
        select one of the multiple audible cues from the sound library;
        alter the selected audible cue to include a harmonic of the sound spectrum of the selected audible cue, the harmonic being non-overlapping with a frequency band in the sound spectrum of the ambient enviornment; and
        cause the altered audible cue to be output with the ambient gain value.

11. The electronic device of claim 10, wherein the electronic device is portable.

12. The electronic device of claim 10, wherein the electronic device is integrated into a vehicle.

13. The electronic device of claim 10, wherein the audible cue is selected based on the sound level of the ambient environment.

14. The electronic device of claim 10, wherein the audible cue is selected from among a first audible cue and a second audible cue based, at least in part, on the sound level of the ambient environment.

15. The electronic device of claim 10, wherein the sound spectrum of the ambient environment comprises a harmonic of the frequency band, and wherein the harmonic of the sound spectrum of the audible cue is non-overlapping with the harmonic of the frequency band.

16. A method of operating an electronic device, comprising:
    determining an ambient sound level of an ambient environment of the electronic device;
    determining an ambient sound spectrum of the ambient environment;
    determining an adjustable gain for an amplifier;
    determining that a frequency band in the ambient sound spectrum of the ambient environment overlaps a sound spectrum of an audible cue;

alter the audible cue to comprise a harmonic of the sound spectrum of an audible cue, the harmonic being non-overlapping with the frequency band; and causing the electronic device to output the altered audible cue into the ambient environment with the adjustable gain.

17. The method of claim 16, further comprising:

selecting the audible cue from a sound library based on the ambient sound spectrum of the ambient environment.

18. The method of claim 16, wherein the audible cue comprises a predetermined sound file.

19. The method of claim 16, wherein the sound spectrum of the ambient environment comprises a harmonic of the frequency band, and wherein the harmonic of the sound spectrum of the audible cue is non-overlapping with the harmonic of the frequency band.

20. The method of claim 17, wherein selecting the audible cue comprises selecting from among a first audible cue and a second audible cue based, at least in part, on one or both of the sound level of the ambient environment and the sound spectrum of the ambient environment.

* * * * *